United States Patent [19]

Nitecki et al.

[11] Patent Number: 4,487,715

[45] Date of Patent: Dec. 11, 1984

[54] METHOD OF CONJUGATING OLIGOPEPTIDES

[75] Inventors: Danute E. Nitecki, San Francisco; Pradip K. Bhatnagar, Santa Clara, both of Calif.

[73] Assignee: The Regents of the University of California, Berkeley, Calif.

[21] Appl. No.: 396,578

[22] Filed: Jul. 9, 1982

[51] Int. Cl.³ ..................... C07C 103/52; C08L 89/00
[52] U.S. Cl. .......................... 260/112.5 R; 525/54.11
[58] Field of Search .............. 260/112.5 R; 525/54.11

[56] References Cited

U.S. PATENT DOCUMENTS

| | | | |
|---|---|---|---|
| 3,317,559 | 5/1967 | Anderson | 260/112.5 R |
| 3,645,996 | 2/1972 | Lee | 260/112.5 R |
| 3,743,628 | 7/1973 | Bodanszky et al. | 260/112.5 R |
| 3,795,666 | 3/1974 | Konig et al. | 260/112.5 R |
| 3,814,732 | 6/1974 | Wang | 260/112.5 R |
| 3,915,949 | 10/1975 | Calescott et al. | 260/112.5 R |
| 3,922,259 | 11/1975 | Sach et al. | 260/112.5 R |
| 3,926,938 | 12/1975 | Hughes et al. | 260/112.5 R |
| 4,060,689 | 11/1977 | Harris | 260/112.5 R |
| 4,062,746 | 12/1977 | Rich | 260/112.5 R |
| 4,062,815 | 12/1977 | Hughes et al. | 260/112.5 R |
| 4,155,914 | 5/1979 | Batz et al. | 260/112.5 R |
| 4,221,777 | 9/1980 | Nishino | 260/112.5 R |
| 4,223,021 | 9/1980 | Momany | 260/112.5 R |
| 4,313,871 | 2/1982 | Bahl | 260/112.5 R |
| 4,350,626 | 9/1982 | Masuko et al. | 260/112.5 R |
| 4,351,762 | 9/1982 | Verlander et al. | 260/112.5 R |
| 4,357,273 | 11/1982 | Masuko et al. | 260/112.5 R |
| 4,379,145 | 4/1983 | Masuko et al. | 260/112.5 R |

Primary Examiner—Delbert R. Phillips
Attorney, Agent, or Firm—Bertram I. Rowland

[57] ABSTRACT

Novel methods are provided for preparing peptide compounds involving functionalizing an available amino group with a carboxy group, esterifying the carboxy group with an hydroxylic compound which forms an ester which is stable under the conditions of cleavage of the oligopeptide from said resin, but which ester is capable of forming a peptide bond with an amino group in an aqueous medium, and without separation, either allowing the oligopeptide to react with itself or with a polypeptide compound.

2 Claims, No Drawings

METHOD OF CONJUGATING OLIGOPEPTIDES

The invention described herein was made in the course of work under a grant or award from the Department of Health and Human Services.

BACKGROUND OF THE INVENTION

1. Field of the Invention

There is an ever increasing need to covalently attach small molecules (haptens, enzyme substrates or inhibitors, reporter groups, etc.) to larger molecules (carriers, enzymes, insoluble matrices, etc.) for a variety of applications (vaccines, antibody production, immunoassays, isolation and separation techniques, etc). In many instances the small molecule is a peptide, which can be synthesized by current methodology. However, the polyfunctional nature of both the peptides and the larger molecule (e.g., proteins) does not allow for precisely controlled covalent attachment. The most commonly used coupling reagents are for the most part bifunctional, with the two functions of equal activity, frequently being the same functionality. Conventional reagents include dialdehydes, carbodiimides, diimidates and diesters, which tend to cross-link the proteins intramolecularly and intermolecularly, resulting in a low efficiency of the desired peptide carrier linkage, as well as substantial modification of the carrier molecules.

Since activation in aqueous media is very nonproductive, the stoichiometry of the conjugation is usually quite poor, i.e., only a small portion of the peptide used becomes attached to the larger molecule. Moreover, it is frequently desirable to know which functional group in the small molecule was utilized for linkage to the larger molecule.

Thus, there is an important need to develop methods which allow a well designed coupling site for the smaller molecule and are stoichiometrically acceptable for the conservation of materials in limited supply.

2. Description of the Prior Art

U.S. Pat. No. 4,127,526 describes the preparation of oligopeptides on chloromethylated resins. 4-Hydroxy-3-nitrobenzenesulfonic acid salt esters are reported in Klausner et al., in Peptides Proceedings of the Fifth American Peptide Symposium, Goodman, M. and Meienhofer, J., eds. John Wiley & Sons, New York, pp. 536–538. The N-9-fluorenylmethyloxycarbonyl (FMOC) is described by Chang et al., Int. J. Peptide and Protein Res. (1980) 15:485–494.

SUMMARY OF THE INVENTION

Method and compositions are provided for preparing activated oligopeptides. A peptide chain is elongated while bound to a solid support, followed by functionalization to form an active ester group which is stable to cleavage from the support. The activated oligopeptide is cleaved from the support and may be used in aqueous media for conjugation to amino group containing polyfunctional molecules, for polymerization or cyclization.

DESCRIPTION OF THE SPECIFIC EMBODIMENTS

In accordance with the subject invention, activated oligopeptides are prepared for conjugation to functionalities capable of forming a stable bond with an active ester group. An amino containing molecule is bound to a support and an oligopeptide chain formed by the successive addition of amino acids. The individual amino acids are appropriately protected and blocking groups removed in accordance with conventional techniques. The resulting oligopeptide, either has an available carboxyl group or a carboxyl group is introduced by bonding an appropriate compound having a carboxyl group with an available functionality, e.g. amino, particularly the terminal amino. The carboxyl group is then further functionalized to provide an active ester which is capable of forming a covalent bond in an aqueous medium. The activated oligopeptide is then cleaved from the column and may be used directly without seperation for covalent bonding to another compound, particularly one having an amino functionality, such as a polypeptide or protein.

In performing the subject method, the reagents which are involved are: (1) the solid support; (2) the amino acids and their appropriate protecting groups, as well as the means for deprotection; (3) the active ester functionality formed from an available carboxy group on the oligopeptide, and as appropriate, a reagent for introducing the carboxy group; (4) cleavage reagents for removing the oligopeptide from the solid support; and (5) reagents for conjugating the activated polypeptide to another molecule. In discussing the subject invention, the various reagents will be considered individually followed by a detailed description of the method.

MATERIALS

Solid Support

The solid support may take any convenient form, such as particles, filters, wall surfaces, or the like. The significant factors for the solid support are its inertness, except for the functionality involved with linking the oligopeptide; ease and manner of removal of the oligopeptide; and absence of non-specific binding. A number of different polymers have found use, particularly latexes, such as polystyrene and polyacrylamides; polyethylene glycol resins, etc. The polymers may be cross-linked to various degrees, usually lightly cross-linked. Alternatively, inorganic materials may be used, such as Bioglas, silicones, etc.

A variety of groups have been employed to provide for cleavable anchor linkages of peptide to the solid support. Included among these groups are chloromethyl, 4-alkoxybenzyl alcohol, benzhydrylamine and the like. Many of the polymers, particularly the modified styrene latexes, are commercially available. Varying numbers of linkage groups per polymer unit are available, but are not critical to this invention.

The amino acids which are employed may be naturally occurring or synthetic. For the most part, the amino acids will be alpha-amino acids, but the amino group need not be at the alpha position and may be at any position. The amino acid may be aliphatic, alicyclic, aromatic or heterocyclic. The amino acids may be of the D- or L- configuration or a racemic mixture.

A wide variety of protective groups may be conjugated to the amino group to provide for the stepwise addition of the amino acids. Illustrative protective groups for protecting amino groups include benzyloxycarbonyl (Z), tert-butyloxycarbonyl (BOC), fluorenylmethyloxycarbonyl (FMOC), isobutyryloxycarbonyl, adamantyloxycarbonyl, o-nitrophenylthiocarbonyl, chloro- or nitrobenzyloxycarbonyl, or the like. The hydroxyl-protecting groups will be for the most part benzyl or tert.-butyl. For carboxyl groups, benzyl or substituted benzyl, e.g., chloro, bromo, or nitro, or tert.-butyl may be employed. The oxy protecting group will provide ethers and esters. In some instances, it may be feasible to employ protective groups, such as sugars, which may be cleaved enzymatically.

The binding of the amino acids to the support, the elongation of the peptide chain, and the removal of the protective groups will follow conventional procedures. Removal of the protective groups may include hydrogenolysis, strong acid catalyzed removal, e.g., trifluoracetic acid, hydrochloric acid, hydrobromic acid, methanesulfonic acid, etc., in an organic non-protic or protic solvent, or other technique, e.g. enzyme catalysed removal.

In some situations, it will be feasible to employ different protective groups, particularly between the alphaamino group and a side chain substituent, where the protective groups may be selectively removed. In this manner, the activated moiety can be conjugated to other than the terminal amino group and at a specific site.

Condensation of the carboxyl group with the deprotected amino group to elongate the oligopeptide will follow conventional conditions, normally employing an activated carboxyl group. The activation may be by use of an activated ester (these esters will be described below), carbodiimide, mixed anhydride, or the like.

The manner of providing the active ester for conjugation of the oligopeptide to another molecule will vary depending upon whether the oligopeptide has an available carboxy group, or such carboxy group must be introduced. Available carboxy groups may be present as a result of including in the oligopeptide aspartic acid, glutamic acid, or other dicarboxylic amino acid which is not conventionally found in naturally occurring polypeptides or proteins. Where there is no carboxyl group, a carboxyl group will have to be introduced. The introduction of a carboxyl group can take many forms, depending upon the manner of linking the carboxy group to the oligopeptide. The conventional functionalities which are available for introduction of the carboxyl functionality will include amino, mercapto and hydroxyl.

By appropriate employment of conventional protecting groups, one can selectively protect a particular functionality to provide for a unique site at which to introduce the carboxy functionality. The carboxy functionality to be subsequently activated will be joined by a linking group to the heteroatom nitrogen, oxygen, or sulphur.

The linking group between the carboxy and the heteroatom will have at least one carbon atom, usually not more than 20 carbon atoms, more usually not more than 10 carbon atoms, generally from about 1 to 6 carbon atoms, and from 0 to 4, usually 0 to 2 heteroatoms, which will be oxygen (as oxy, that is hydroxy or ether), nitrogen (amino or amido, free of reactive hydrogens) and sulfur (thiol or thioether). The linking group may be aliphatically saturated or unsaturated, usually having not more than one site of aliphatic unsaturation, e.g., ethylenic. The linking group may be aliphatic, aromatic, alicyclic or heterocyclic.

Where an amino group is the configuration site, the functionalization of the peptide chain with an activated ester is readily and preferably achieved by conjugation of a cyclic anhydride, which cyclic anhydride may be aliphatic, alicyclic, aromatic or heterocyclic. In most instances, the aliphatic anhydrides will find use, although in special situations 1,2-dicarboxylic acids bonded to a ring may find use. For the most part, the dibasic carboxylic acids will have from 4 to 20 carbon atoms, more usually from 4 to 12, and preferably from about 4 to 8 carbon atoms. The dicarboxylic acids may be substituted with a variety of functional groups, such as oxy (hydroxy or ether), cyano, halo, nitro, amino, (including alkyl substituted) amido, or the like.

Illustrative anhydrides include succinic anhydride, glutaric anhydride, phthalic anhydride, 1,2-cyclohexanedicarboxylic acid anhydride, 4-nitrophthalic anhydride, 2-2,dimethyl-4,5-dicarboxy-1,3-dioxacyclopentane, maleic anhydride, N-methyl 2,3-dicarboxyindole anhydride, etc.

Besides cyclic anhydrides mono-activated dicarboxylic acids may be employed where the dicarboxylic acid is esterfied stepwise: once before conjugation to the oligopeptide and then after conjugation to the oligopeptide.

Rather than carboxyl groups, other acyl groups may be used such as sulfonyl halides, phosphonyl halides, etc., where such acyl group would offer a synthetic advantage or impart a desirable property to the oligopeptide.

With acyl groups, the basic character of the amino group is lost. In the case of the N-terminal amino group, this may be desirable. However, for an amino group or an internal amino acid it may be desirable to retain the basic character of the amino group. Various procedures known in the literature may be used for linking a carboxy group to an amino group. Activated halo groups may be employed, particularly iodo and bromo, as in iodoacetic acid and α-bromopropionic acid. Reductive amination may be employed where an imine is formed with an aldehyde and the imine then reduced with a metal hydride, e.g., cyanoborohydride. Illustrative compounds include carboxyacetaldehyde, glucuronic acid, galacturonic acid, 5-carboxypentanal, 3-carboxyacrylaldehyde, and carboxymethoxyacetaldehyde The carboxylic acid (including anhydride) compounds that are employed should be free of groups which interfere with the conjugation of the carboxylic acid compounds to the oligopeptide and the formation of the activated ester. This may be as a result of the absence of such groups or the presence of protective groups which may be removed in conjunction with cleavage from the support or be removed in a separate step from such cleavage.

Where mercaptide groups are involved, one may use active halides, olefins such as are present in acrylic acid, or reagents having a carboxy group and capable of forming a disulphide with a mercaptide group.

With hydroxyl groups, ethers will be formed, normally with active halides or active esters.

After providing for the carboxylic acid group, the free carboxyl group is activated to form an active ester. With the cyclic anhydride, the half amide acid (amic acid) is formed. By active ester is intended an ester which is capable of forming a covalent, usually a peptide, bond in an aqueous medium. Usually the bond will be to a functionality normally present in a polypeptide. Various hydroxyl componds have been employed to form these esters. These hydroxyl compounds are illustrated by N-hydroxy succinimide, pnitrophenol, pentachlorophenol and 4-hydroxy-3-nitrobenzenesulfonic acid sodium salt.

Cleavage from the support may be achieved in a variety of ways, depending upon the particular support. Conveniently, hydrogen fluoride or trifluoroacetic acid may be employed or hydrogenolysis, where the active ester group is retained and the oligopeptide separated from the support.

METHOD

In performing the subject method, the first step is to conjugate the initial amino acid to the support. The particular linkage will be capable of surviving the procedures employed in elongating the peptide chain. For the most part esters will be formed, the conditions varying with the reactive functionality present on the support. Conventional conditions are employed in accordance with those suggested by the commercial supplier of the resin.

The peptides are prepared using standard solid-phase techniques. The synthesis is commenced from the C-terminal end of the peptide, using an alpha-amino protected amino acid. The resin can be prepared by attaching the required alpha-amino acid to a chloromethylated resin or an hydroxymethyl resin or benzhydrylamine resin, an exemplary chloromethylated resin is sold under the trade name BIO-BEADS XF-1 by Bio-Rad Laboratories, Richmond, California. The preparation of an exemplary hydroxymethyl resin is described by Bodonszky et al., Chem.Ind. (London) 38, 1597 (1966).

The alpha-amino protected amino acid can be coupled to the chloromethylated resin according to the method described by Gisin, Helv. Chim. Acta 56, 1476 (1973). Conveniently, cesium bicarbonate may be employed. The alpha-amino protecting group may then be removed by any conventional technique, such as trifluoroacetic acid or hydrogen chloride in an organic solvent at room temperature. After removal of the alpha-amino protecting group, the remaining protected amino acids are added stepwise in the desired order. Each protected amino acid is generally reacted in a three-fold excess using an appropriate carboxyl group activator, such as an organic solvent soluble carbodiimide e.g. dicyclohexyl diimide in a mixed solvent, e.g., methylene dichloride-dimethyl formamide.

For further description of synthetic methods, including methods of deprotection of amino groups see Barany and Merrifield, Solid-Phase Peptide Synthesis "The Peptides, Analysis, Synthesis, Biology," Special Methods in Peptide Synthesis, Part A, Vol. 2, Gross and Meienhofer, Eds., Academic Press, New York, 1980, pages 1-284; Chang et al., Int. J. Peptide Protein Research (1980) 15: 485-494; Meienhofer et al., Ibid (1979) 13:35-42.

After completion of the synthesis of the desired oligopeptide, the oligopeptide may be partially or completely deprotected while retaining the linkage to the resin. Where a carboxy group is present in an oligopeptide, it will normally be present in protected form and may be deprotected to provide the desired carboxyl functionality. Where the carboxyl group to be activated is present on the oligopeptide it will be deprotected. Where a carboxyl group is not protected, one other functionality will be deprotected for linking of the carboxyl functionality. There will be one functionality which will be preferentially conjugated to the carboxy group. By using different protective groups, one can preferentially remove one protective group as distinguished from another. Protective groups present on a carboxylic acid present in the oligopeptide may or may not be retained, depending upon the activity of the particular carboxylic acid. Where the carboxylic acid is relatively unreactive, it may be deprotected, but where it will compete with the carboxylic acid which is introduced, the protective group will not only be retained, until at least the active ester is formed, but potentially after reaction of the active ester to form the final product.

Deprotection may involve acids of varying degrees of acidity, based upon the particular acid and the solvent system, bases, of various degrees of basicity, which may include hydroxylic bases, tertiary amines, and the like, where aqueous or non-aqueous systems are employed. Protective groups for carboxyl may include nitrobenzyl, benzyl, tert.-butyl, or other esters. Besides hydrolytic techniques, hydrogenolysis may also be employed.

Where a carboxyl group is to be introduced, the partially or completely deprotected oligopeptide bound to the resin may now be employed for functionalization. The particular conditions for functionalization will vary with the compound used and the functionality which reacts with the group on the oligopeptide with an amino group when employing cyclic anhydrides, at least one equivalent per equivalent of oligopeptide will be used, usually at least 2, and amounts of 10 equivalents or more may be used, although greater excesses are usually not desirable. An inert organic solvent is normally employed, conveniently a halo-hydrocarbon. The reaction is carried out under mild conditions, generally ambient temperatures, desirably in the presence of a catalyst e.g., 1-hydroxybenzotriazole. After sufficient time for the reaction to occur, the resin may be isolated and purified or may be used directly.

For reductive amination, the aldehyde-acid may be added to the resin in a polar organic solvent, e.g., alkanol, at a pH approaching neutrality or neutrality and after sufficient time for formation of the imine, the solution is made mildly basic, about pH 7.2 to 7.5 and cyanoborohydride added in mild excess. Reduced temperatures are normally employed and the reaction allowed to proceed to completion.

In individual situations, haloalkylesters may be employed in the presence of a polar organic solvent, particularly in the presence of a tertiary amine.

After completion of the introduction of the carboxyl group, the resin may now be washed, conveniently by repetitive washes with inert solvents to remove the excess of the other reactants and any materials which are nonspecifically adhered to the resin. The washed resin may then be combined with an appropriate hydroxylic compound for preparation of the ester. The ester is conventionally prepared employing a polar carbodiimide in an inert organic solvent, e.g., DMF and/or $CH_2Cl_2$, where the activating carbodiimide and hydroxylic compound are used in excess, usually at least two-fold excess and usually less than about 5-fold excess. Ambient conditions may be employed and the reaction allowed to proceed until completion. The resulting products may then be further purified, conveniently by washing with inert solvents, and the product dried.

Significant to the subject invention is the manner in which the oligopeptide is cleaved from the resin. The conditions employed must distinguish between the ester linkage to the resin and the activated ester to be employed for further reaction. Particularly, a strong acid is employed at mild temperatures, generally from about $-20°$ to $30°$ C., more usually from $0°$ to about $25°$ C., in an inert organic solvent, particularly an aromatic solvent, more particularly an aromatic ether of from about 7 to 10 carbon atoms. Of particular interest as acids are those which cannot react to form a covalent product with the various functionalities present in the oligopeptide. These acids are particularly exemplified by hydrofluoric acid and trifluoroacetic acid. Relatively small amounts of the acid may be added, since the acid serves a catalytic role. After the addition of the acid, the reaction may then proceed for sufficient time for the oligopeptide to be cleaved from the resin.

The resulting slurry may then be used directly for reaction of the oligopeptide. The slurry is combined with the appropriate other reactant or may react with itself, intramolecularly or intermolecularly in an aqueous medium, generally at a mildly basic pH, e.g. 8–10. The acid is conveniently neutralized with a mild base e.g. borate carbonate, phosphate, etc. The product may then be isolated and purified in accordance with conventional techniques, e.g., chromatography, electrophoresis, etc. The oligopeptides may be used for a wide variety of purposes. Internal cyclization can lead to products having physiological activity, tyrocidine, gramicidin S, and the like. The oligopeptide may be polymerized to provide a repeating unit, which may be used in affinity columns, as immunogens, and the like. Alternatively, the oligopeptide may be used as a hapten and conjugated to an immunogen to produce antibodies recognizing a specific determinant site of a polypeptide or protein of interest. Various common immunogens include bovine serum albumin, bovine gamma-globulin, keyhole limpet hemocyanin, or the like.

The following examples are offered by way of illustration and not by way of limitation.

EXPERIMENTAL

The following abbreviations will be used having the indicated definitions: Boc, tert.-butyloxycarbonyl; DNP, 2,4-dinitrophenyl; FMOC, N-9-fluorenylmethoxycarbonyl; BSA, bovine serum albumin; OSu, N-hydroxy succinimide; ONp, p-nitrophenyl; PCP, pentachlorophenyl; HNSA, 4-hydroxy-3-nitrobenzene sulfonic acid sodium salt; (P), polymeric resin.

The peptide, Boc-Lys-($\epsilon$-DNP)-Ala-(P)((P) in this example is chloromethyl resin) was synthesized and amino group deprotected and neutralized by standard methods (Barany and Merrifield) supra. The resin (5 g 0.32 mm Cl/g of peptide as determined by Ala substitution; 1.6 meq total) was dispended in $CH_2Cl_2$ and treated with 8 meq of succinic anhydride (800 mg) and a catalyst, 1-hydroxybenzotriazole hydrate (1.08 g, 8 meq) with mixing. After three hours, the polymer was washed $5 \times CH_2Cl_2$; $5 \times DMF$; $5 \times CH_2Cl_2$ (about 35 ml each). A 100 mg aliquot of the polymer was taken and analyzed by high voltage electrophoresis and shown to have the expected properties. The remaining polymer was divided into approximately four equal portions for reaction with different hydroxylic compounds. The following table indicates the particular hydroxylic compound which was used and the amount.

TABLE I

| Hydroxyl Compound[1] | mg | mmoles | Solvent[2] | ml | EDC[3] mg | mmoles |
|---|---|---|---|---|---|---|
| HNSA | 970 | 4 | DMF | 30 | 786 | 4 |
| PCP | 1064 | 4 | $CH_2Cl_2$ | 20 | 768 | 4 |
| OSu | 461 | 4 | $CH_2Cl_2$ | 20 | 768 | 4 |
| ONp | 557 | 4 | $CH_2Cl_2$ | 20 | 768 | 4 |

TABLE I-continued

[1]HNSA — 4-hydroxy-3-nitrobenzene sulfonic acid.
PCP — pentachlorophenol
OSu — N—hydroxy succinimide
$ON_p$ — p-nitrophenol
[2]DMF — N,N—dimethyl formamide
$CH_2Cl_2$ — dichloromethane
[3]EDC — 1-ethyl-3-(3''-dimethylaminopropyl) carbodiimide hydrochloride The four preparations were allowed to react for 24 hours at room temperature and the resins were then washed with about 30 ml each $5 \times CH_2Cl_2$; $5 \times DMF$; and $5 \times CH_2Cl_2$. These preparations were dried in in vacuo and then used directly for cleavage of the oligopeptide from the resin.

Each of the above prepared resins (200 mgs each) were suspended and stirred in 2 ml anisole cooled to $-70°$ C. (dry ice/acetone) and purged with nitrogen. An HF lecture bottle valve was opened for one minute and HF was allowed to condense into the sample. The cooling bath was then changed to ice water and the temperature allowed to rise for about two hours to a final temperature of ambient temperature, while maintaining a nitrogen atmosphere. The resulting slurry was then extracted with diethyl ether and suspended directly between layers of 5 ml of borate buffer, pH 8.5, containing 30 mg of BSA and 10 ml of ether. After decanting the ether layer, the protein solution was stirred overnight, filtered, dialyzed extensively for several days against buffer, and chromatographed on Sephadex G-25 column to remove unreacted peptide. Excellent yields were obtained with substantial recovery of any unreacted protein.

The resulting product could be used as an immunogen conjugate for producing antibodies to the oligopeptide.

In the next example, the peptide FMOC-Lys ($\epsilon$-DNP)-Ala-(P)((P) is the 4-alkoxybenzyl resin) was synthesized and deprotected by previously described methods for this resin. (See Chang et al., supra and Meienhoffer et al., supra.) Four separate portions (500 mg) of the above indicated resin, substituted at a concentration of 0.133 moles/g were succinylated, washed and derivatized with the previously indicated hydroxy compounds in substantially the same manner as described for the chloromethyl resin. The activated peptide resins were treated with 20 ml of 40% trifluoroacetic acid in $CH_2Cl_2$ for 1 hr. The resin was filtered off, the solvent removed in vacuo and the residue treated with 0.1 N borate buffer, pH 8.5, containing 76 mg of BSA. The resulting product was worked up as described above.

Substantially the same results were obtained with the 4-alkoxybenzyl resin employed in this example as was obtained in the chloromethyl resin example described previously.

In the next example, a fragment of a viral structural protein (H-Ile-Pro-Ile-Pro-Ser-Ser-Trp-Ala-Phe-[P]) was synthesized, deprotected and neutralized on chloromethyl resin as described previously. One gram of the resin containing 0.3 mmoles of the peptide was suspended in 15 ml of $CH_2Cl_2$, 150 mg of succinic anhydride added and the mixture stirred overnight at room temperature. The resulting product was washed with 15 ml each time $5 \times CH_2Cl_2$; $5 \times DMF$; $5 \times CH_2Cl_2$. The succinylated resin was suspended in $CH_2Cl_2$(15 ml) and 256 mg of PCP and 190 mg EDC added. After stirring for 6 hours, the resin was washed 15 ml each time 5×CH$_2$Cl$_2$ and dried in vacuo.

The activated peptide resin (200 mg) was cleaved using the mild HF treatment described previously. The mixture of the cleaved resin, peptide and anasole was suspended between the layers of 5 ml of 0.1N borate buffer, pH 8.2, containing 10 mg of keyhole limpet hemocyanin, and 5 ml of diethyl ether. The ethereal layer was decanted and an additional 10 ml of ether added. After stirring the mixture overnight in the cold (4° C.), the layers were separated, the aqueous layer dialyzed against phosphate buffered saline, pH 7.2, and used for immunization. In a repeat of the above experiment, employing $^{14}$C labeled succinic anhydride, 0.83 mg of the peptide was found attached to 10 mg of the protein.

In a similar fashion several peptides were synthesized, activated, cleaved from the polymer and attached to carrier proteins. The following is a list of such peptides:
  a. Cys-Thr-Lys-Pro-Thr-Asp-Gly-Asn-Cys.
  b. (a)-Thr-Cys-Ile-Pro-Ile-Pro-Ser-Ser-Trp-Ala-Phe.
  c. Gly-Asn Cys-Thr-Cys-Ile-Pro-Ile-Pro-Ser-Ser-Trp-Ala-Phe.
  d. Thr-Lys-Pro-Thr-Asp-Gly-Asn-Cys-Thr-Cys-Ile-Pro-Ile-Pro-Ser-Ser-Trp-Ala-Phe.

In the next example, employing chloromethyl resin, substituted with Boc-Ala-OH(0.32 meq/g), the Ala was sequentially coupled with Boc-Lys-($\epsilon$-DNA)-OH employing substantially the same conditions as described above. The mild HF treatment previously described yielded 0.24 mmoles of succinyl-Lys ($\epsilon$-DNP)-Ala-OH per g (75% yield based on alanine). Four 200 mg portions of the peptide resin containing succinylated peptide were treated with six-fold excesses of the hydroxy compounds listed in Table I. After appropriate washes and work up as described previously, the resin was cleaved by mild HF treatment and after diethyl ether washes, the peptide-resin mixture was directly treated with 7 ml of 0.1N borate buffer containing 30 mg BSA and the pH adjusted to 8.5. The calculated molar ratio of activated peptide per lysine residue in BSA was 1.8. The protein solution was filtered, dialyzed extensively, and chromatographed on Sephadex G15 in 0.1N ammonia to remove traces of unreacted peptide. The protein recoveries were nearly quantitative.

In the next example, 4-alkoxybenzyl alcohol resin was employed and the same peptide as in the above example was synthesized using FMOC derivatives, FMOC-Ala as the first attachment, followed by FMOC-Lys($\epsilon$-DNP)OH and succinic anhydride.

Portions of dried resin were cleaved with TFA/CH$_2$Cl$_2$ and found to yield under isocratic conditions, 0.133 mmoles peptides per gram of resin. Four separate portions of 500 mg of resin where derivatized to form the esters previously described in Table I. The esters were cleaved with TFA/CH$_2$Cl$_2$, filtered off, the resin dried and the residue treated with 10 ml of 0.1N borate buffer, pH 8.5 containing 76 mg BSA. The calculated ratio of activated peptide to lysine groups in BSA was 1. The reacted protein was treated as above and results are shown in the following Table II:

TABLE II

| Ester used | Chloromethyl resin mild HF cleavage, Boc-System[a] | | 4-Alkoxybenzyl alcohol resin[b], TFA cleavage, FMOC-system | |
|---|---|---|---|---|
| | Moles DNP Substituted/ Mole BSA | Efficiency of coupling (% of reagent utilized) | Moles DNP substituted/ Moles BSA | Efficiency of coupling (% of reagent utilized) |
| HNSA | 2 | 2.8 | 3 | 4.9 |
| Pcp | 16 | 14.8 | 12 | 19.8 |
| OSu | 4 | 3.6 | 8 | 13.2 |
| ONp | 1 | 0.9 | 2 | 3.3 |

[a]Starting ratio of peptide to Lys of BSA was 1.8:1.
[b]Starting ratio was 1:1.

It is evident from the above results, that a simple rapid and efficient method is provided for conjugating polypeptides to a protein. The method permits substantially quantitative utilization of the usually scarce and expensive protein reagent, so that economic conjugations are achieved. Furthermore, the reagents used are simple and allow for retention of the natural structure and conformations of the protein conjugate. Also, the particular site of conjugation of the peptide can usually be selected by employing appropriate protection and deprotection means known in the art. The carboxyl group which is used for forming peptide bonds is a particularly convenient functionality, which can be readily activated by employing an ester capable of forming peptide bonds in an aqueous medium. The method does not involve any separation step from the resin which is employed, until after the conjugation has been performed, at which time, the resin is easily removed from the product.

Because of the controlled addition and protection, the method provides for preparation of concatemers of peptides, as well as intramolecular cyclization. These compounds can find a variety of uses in mimicking naturally ocurring compounds, in providing novel polymers of repeating sequences, and the like.

Although the foregoing invention has been described in some detail by way of illustration and example for purposes of clarity of understanding, it will be obvious that certain changes and modifications may be practiced within the scope of the appended claims.

What is claimed is:

1. An improved method for preparing a polypeptide product capable of forming a peptide bond in an aqueous medium, said method being of the type wherein an oligopeptide is formed by the sequential addition of amino acids to an initial amino acid which is bound to a 4-alkoxybenzyl alcohol resin or chloromethyl resin through an ester linkage, said improvement comprising:
  reacting a cyclic carboxylic acid anhydride with an available amino group on the oligopeptide to form an amic acid to provide a single free reactive carboxyl group on said oligopeptide;
  esterifying said carboxyl group with an hydroxyl compound selected from the group consisting of 4-hydroxy-3-nitrobenezesulfonic acid salt, pentachlorophenol, N-hydroxy succinimide, and p-nitrophenol to provide an activated ester stable to cleavage of the oligopeptide from the resin and capable of forming a peptide bond in an aqueous medium;
  cleaving said oligopeptide from said resin employing hydrofluoric acid or trifluoroacetic acid in an inert organic solvent to provide a mixture of said resin and said oligopeptide in an acid solution;
  neutralizing said acid solution to a mildly basic pH in the absence or presence of a peptide having an available amino group, whereby said oligopeptide reacts either (1) intramolecularly or intermolecularly with itself or (2) with said amino containing peptide to form a peptide bond.

2. A method according to claim 1, where said anhydride is succinic anhydride.

* * * * *